(12) United States Patent
Farris et al.

(10) Patent No.: US 8,840,669 B2
(45) Date of Patent: Sep. 23, 2014

(54) VARIABLE HEIGHT INTERVERTEBRAL DEVICES AND METHODS FOR USE

(75) Inventors: Jeffrey A. Farris, Berne, IN (US); Daniel Refai, Atlanta, GA (US)

(73) Assignee: Biomet Spine, LLC, Broomfield, CO (US)

( * ) Notice: Subject to any disclaimer, the term of this patent is extended or adjusted under 35 U.S.C. 154(b) by 179 days.

(21) Appl. No.: 13/258,824

(22) PCT Filed: Apr. 13, 2010

(86) PCT No.: PCT/US2010/030896
§ 371 (c)(1),
(2), (4) Date: Oct. 11, 2011

(87) PCT Pub. No.: WO2010/120782
PCT Pub. Date: Oct. 21, 2010

(65) Prior Publication Data
US 2012/0022654 A1    Jan. 26, 2012

Related U.S. Application Data

(60) Provisional application No. 61/168,829, filed on Apr. 13, 2009.

(51) Int. Cl.
*A61F 2/44* (2006.01)
*A61F 2/30* (2006.01)
*A61F 2/46* (2006.01)

(52) U.S. Cl.
CPC ......... *A61F 2/44* (2013.01); *A61F 2002/30892* (2013.01); *A61F 2310/00029* (2013.01); *A61F 2002/3055* (2013.01); *A61F 2220/0033* (2013.01); *A61F 2/30744* (2013.01); *A61F 2002/30495* (2013.01); *A61F 2002/30523* (2013.01); *A61F 2310/00017* (2013.01); *A61F 2002/4475* (2013.01); *A61F 2/442* (2013.01); *A61F 2002/30904* (2013.01); *A61F 2002/30411* (2013.01); *A61F 2002/30372* (2013.01); *A61F 2002/30841* (2013.01); *A61F 2002/3052* (2013.01); *A61F 2220/0025* (2013.01); *A61F 2002/30405* (2013.01); *A61F 2002/4629* (2013.01); *A61F 2/4611* (2013.01); *A61F 2310/00023* (2013.01); *A61F 2002/30331* (2013.01); *A61F 2002/30601* (2013.01)
USPC ........................................................ 623/17.16

(58) Field of Classification Search
USPC .......... 623/17.11–17.16; 403/43–48; 254/103
See application file for complete search history.

(56) References Cited

U.S. PATENT DOCUMENTS

| | | | |
|---|---|---|---|
| 5,458,641 A | 10/1995 | Ramirez Jimenez | |
| 5,916,267 A * | 6/1999 | Tienboon | 623/17.11 |

(Continued)

FOREIGN PATENT DOCUMENTS

DE         10127924 C1    12/2002

OTHER PUBLICATIONS

Kossmann T. et al. (Dec. 19, 2002). DE 101 27 924 Machine Translation.*

(Continued)

*Primary Examiner* — Michael T Schaper
*Assistant Examiner* — Tracy Kamikawa
(74) *Attorney, Agent, or Firm* — Harness, Dickey

(57) ABSTRACT

Variable height intervertebral devices and method of employing the devices are disclosed. The devices and methods can maintain or re-establishing anatomic spacing along a spine and can ensure avoidance of long-term structural, neurological, vascular, and/or other systemic impairments. The intervertebral device includes a cylindrical body having a first end and a second end opposite the first end; a first disk threaded to the first end of the cylindrical body and a second disk mounted to the second end of the cylindrical body; means for rotating the cylindrical body whereby the first disk translates along the cylindrical body to vary the height of the device; and a plurality of pins mounted to one disk, the plurality of pins slidably engageable with a plurality of sleeves mounted to the other disk, the pins and sleeves inhibiting the first disk from rotating when the cylindrical body is rotated.

20 Claims, 19 Drawing Sheets

(56) References Cited

U.S. PATENT DOCUMENTS

| | | | |
|---|---|---|---|
| 6,015,436 A | 1/2000 | Schoenhoeffer | |
| 7,056,343 B2 * | 6/2006 | Schafer et al. | 623/17.11 |
| 2004/0153160 A1 * | 8/2004 | Carrasco | 623/17.15 |
| 2004/0172129 A1 | 9/2004 | Schafer et al. | |
| 2004/0186569 A1 * | 9/2004 | Berry | 623/17.11 |
| 2006/0058877 A1 | 3/2006 | Gutlin et al. | |
| 2007/0191954 A1 * | 8/2007 | Hansell et al. | 623/17.15 |
| 2008/0243254 A1 * | 10/2008 | Butler | 623/17.16 |

OTHER PUBLICATIONS

International Search Report for PCT/US2010/030896 dated Nov. 5, 2010.

International Preliminary Report on Patentability (IPRP) for corresponding PCT application No. PCT/US2010/030896, mailed Oct. 18, 2011.

* cited by examiner

VARIABLE HEIGHT INTERVERTEBRAL DEVICES AND METHODS FOR USE

CROSS-REFERENCE TO RELATED APPLICATIONS

This application is a national stage filing under section 371 of International Application No. PCT/US2010/030869 filed on Apr. 13, 2010, and published in English on Oct. 20, 2010 as WO 2010/120728 and claims priority of U.S. Provisional application No. 61/168,829 filed on Apr. 13, 2009, the entire disclosure of these applications being hereby incorporated herein by reference.

BACKGROUND OF THE INVENTION

1. Field of the Invention

The present invention relates generally to spinal orthopaedic and neurosurgical implants used for insertion within a space between vertebrae. More specifically, but not exclusively, the present invention concerns adjustable intervertebral devices that can be used to replace a resected, fractured, or diseased portion of the spine to maintain or re-establish proper spacing between vertebrae.

2. Description of Related Art

Damage or disease that affects the integral structure of vertebrae in a spinal column may lead to neurologic impairment or loss of structural support integrity. Such damage or disease can lead to permanent damage to the surrounding soft tissue and adjacent neurologic, vascular, and systemic structures. Maintaining or re-establishing anatomic spacing within a spine can be critical to ensuring continued functionality and mobility of the patient and avoidance of long term serious structural, neurological, vascular, and/or other systemic impairments.

Aspects of the present invention provide adjustable, intervertebral devices and methods that can maintain or re-establish anatomic spacing within a spine.

SUMMARY OF ASPECTS OF THE INVENTION

Aspects of the present invention restore or maintain the spacing between vertebrae by providing intervertebral devices that can vary in height during installation by the surgeon. Aspects of the invention are marketed under the name "Expandable Interbody Fusion Device."

One embodiment of the present invention is a variable height intervertebral device comprising or including a cylindrical body having a first end and a second end opposite the first end; a first disk threaded to the first end of the cylindrical body and a second disk mounted to the second end of the cylindrical body; means for rotating the cylindrical body whereby the first disk translates along the cylindrical body to vary a height of the device; and a plurality of pins mounted to one of the first disk and the second disk, the plurality of pins slidably engageable with a plurality of sleeves mounted to the other of the first disk and the second disk, the pins and sleeves inhibiting the first disk from rotating when the means for rotating rotates the cylindrical body. In one aspect, the means for rotating the cylindrical body comprises at least one projection positioned between the first end and the second end of the cylindrical body, for example, a plurality of circumferential teeth. In another aspect, the device may further include a first vertebra engagement member or end cap mounted to the first disk and a second vertebra engagement member or end cap mounted to the second disk, for example, plastic or elastomeric end caps. In another aspect, the device may further include means for limiting translation of at least the first disk. In one aspect, the device may be infinitely variable in height. In another aspect, the variability of the length of the device is achieved by moving or translating both ends of the device, that is, the device may provide bi-directional adjustment.

Another embodiment of the of the invention is a method for separating or maintaining vertebrae comprising or including inserting the device recited above between a first vertebra and a second vertebra; and rotating the cylindrical body whereby at least the first disk axially translates along the cylindrical body between the first vertebra and the second vertebra. In one aspect, the method may further include limiting the axial translation of the first disk along the cylindrical body. In another aspect, the method may include inhibiting the first disk from rotating when the means for rotating rotates the cylindrical body. The means for rotating the cylindrical body may include a plurality of circumferential teeth positioned about the cylindrical body, and wherein rotating the cylindrical body may be practiced by engaging at least one of the teeth with a pinion mounted to a tool and deflecting the at least one tooth in a circumferential direction by rotating the pinion.

A further embodiment of the invention is a variable height intervertebral device comprising or including a hollow cylindrical body having a threaded first end and a threaded second end opposite the threaded first end; a first disk internally threaded to the first end of the cylindrical body and a second disk internally threaded to the second end of the cylindrical body; a first end cap mounted to the first disk and a second end cap mounted to the second disk; means for rotating the cylindrical body whereby the first disk axially translates along the cylindrical body and impels the first end cap into engagement with a first vertebra and the second end cap into engagement with a second vertebra; and a plurality of pins mounted to one of the first disk and the second disk slidably engageable with a plurality of sleeves mounted to other of the first disk and the second disk, the plurality of pins and the plurality of sleeves inhibiting the first disk from rotating when the means for rotating rotates the cylindrical body. In one aspect, the means for rotating the cylindrical body comprises at least one projection, but typically a plurality of gear teeth, positioned between the first end and the second end of the cylindrical body, the at least one projection engageable by a tool. In another aspect, the plurality of pins comprises at least two pins and the plurality of sleeves comprises at last two sleeves. In another aspect, the device may also include a housing surrounding the cylindrical body, and wherein the device may further include at least one projection on the first end cap positioned to engage a recess in the housing to limit translation of the first disk and/or the second disk.

Details of these aspects of the invention, as well as further aspects of the invention, will become more readily apparent upon review of the following drawings and the accompanying claims.

BRIEF DESCRIPTION OF THE FIGURES

The subject matter that is regarded as the invention is particularly pointed out and distinctly claimed in the claims at the conclusion of the specification. The foregoing and other objects, features, and advantages of the invention will be readily understood from the following detailed description of aspects of the invention taken in conjunction with the accompanying drawings, in which:

FIGS. 23A, 23B, 23C, and 24D are cross sectional views similar to FIG. 22 illustrating the sequential engagement of an end cap with housing according to one aspect of the invention.

DETAILED DESCRIPTION OF FIGURES

Figure 1:
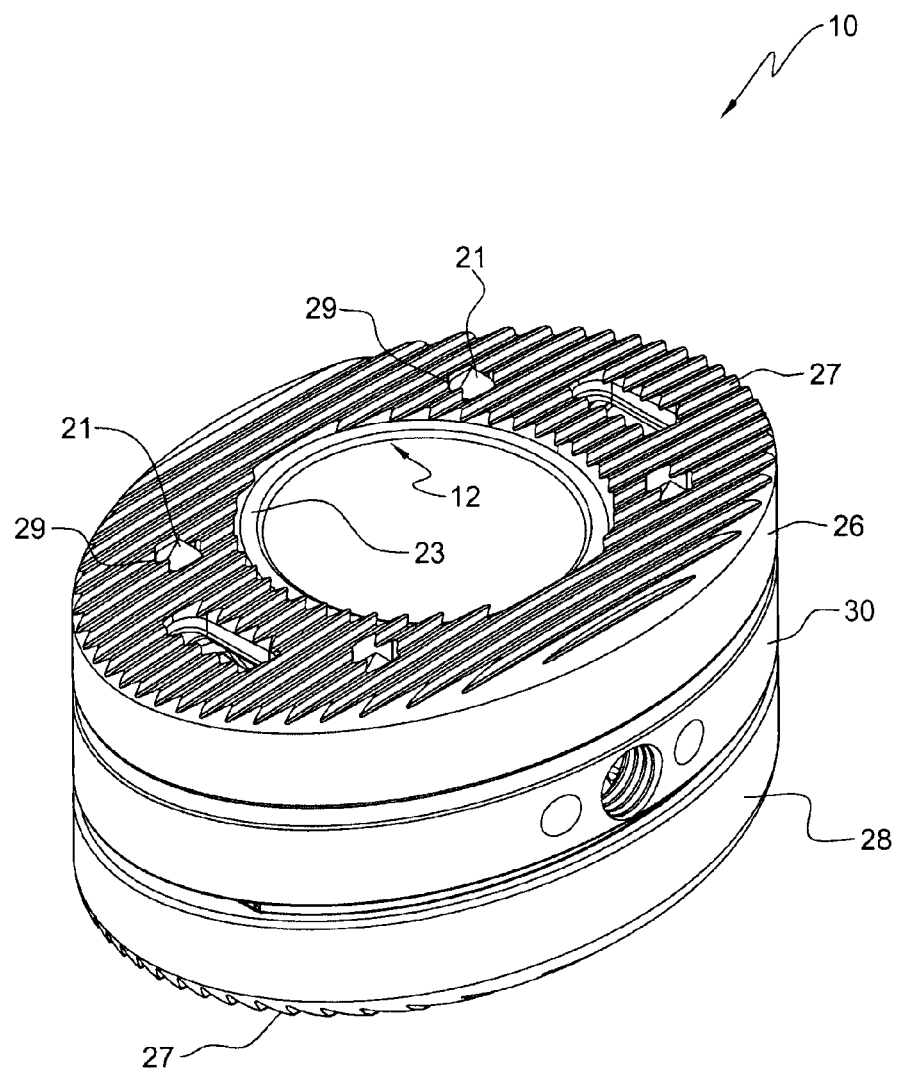
FIG. 1 is a perspective view of an intervertebral device according to one aspect of the invention.
Figure 2:
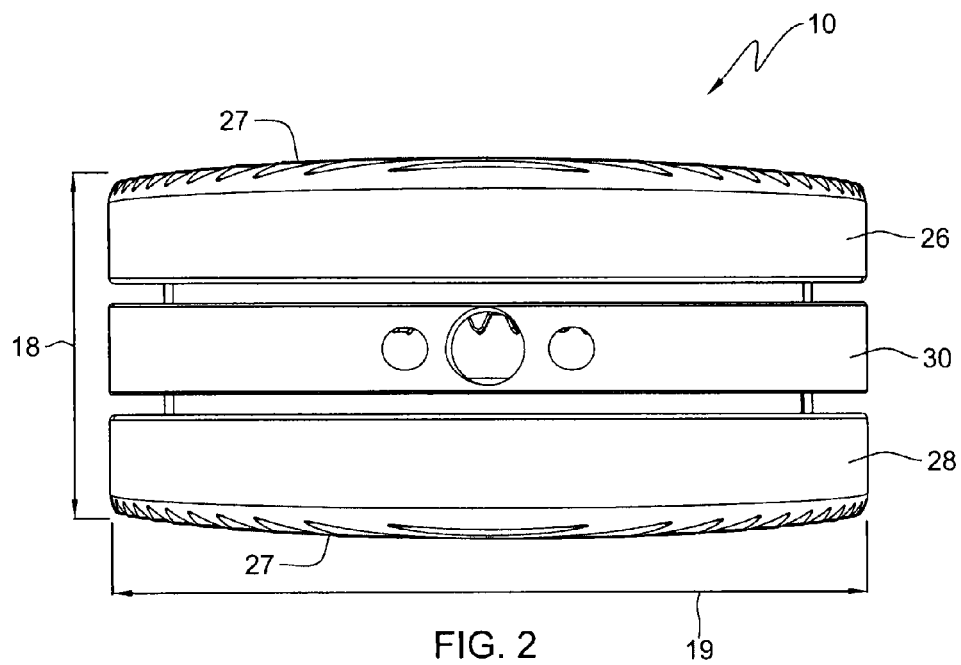
FIG. 2 is a front elevation view of the intervertebral device shown in FIG. 1.
Figure 3:
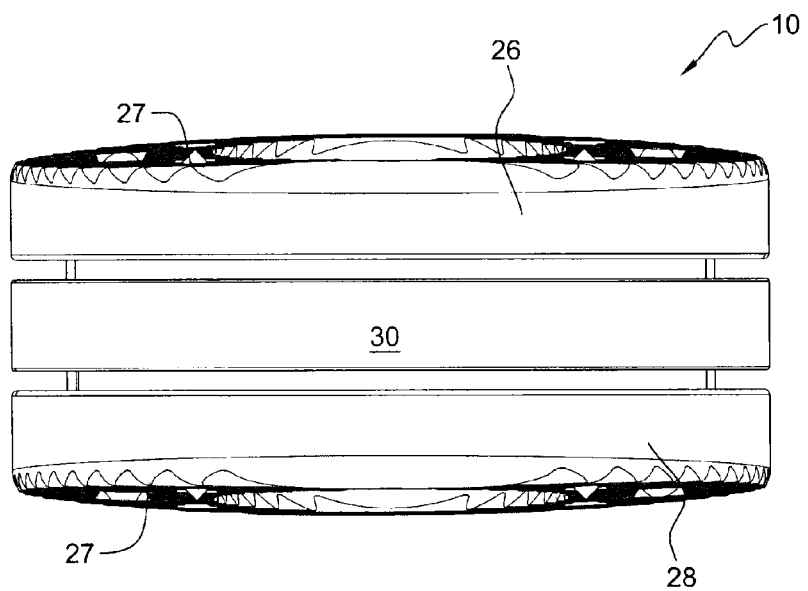
FIG. 3 is a rear elevation view of the intervertebral device shown in FIG. 1.
Figure 4:
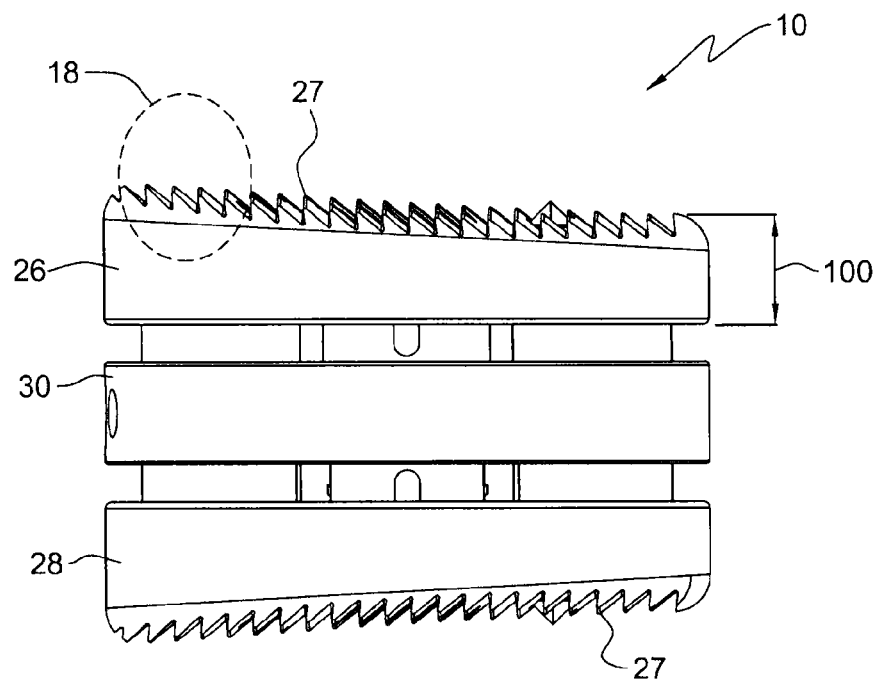
FIG. 4 is a right side elevation view of the intervertebral device shown in FIG. 1.
Figure 5:
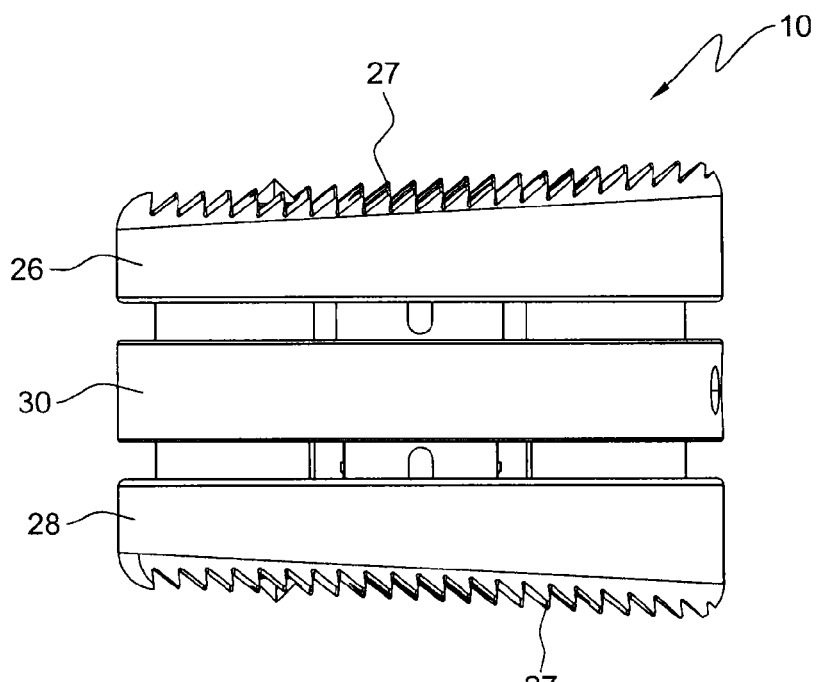
FIG. 5 is a left side elevation view of the interverbral device shown in FIG. 1.
Figure 6:
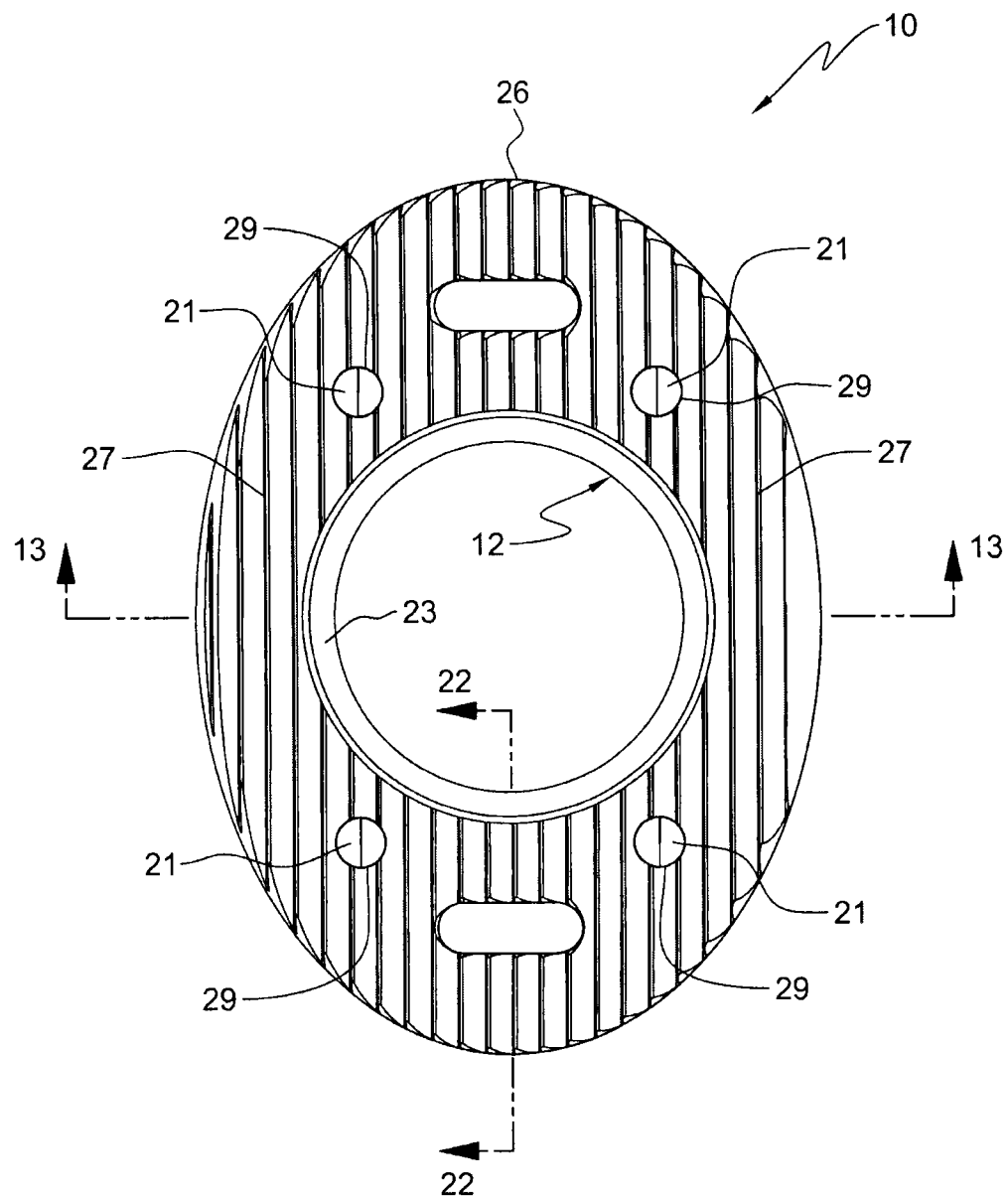
FIG. 6 is a top plan view of the intervertebral device shown in FIG. 1.
Figure 7:
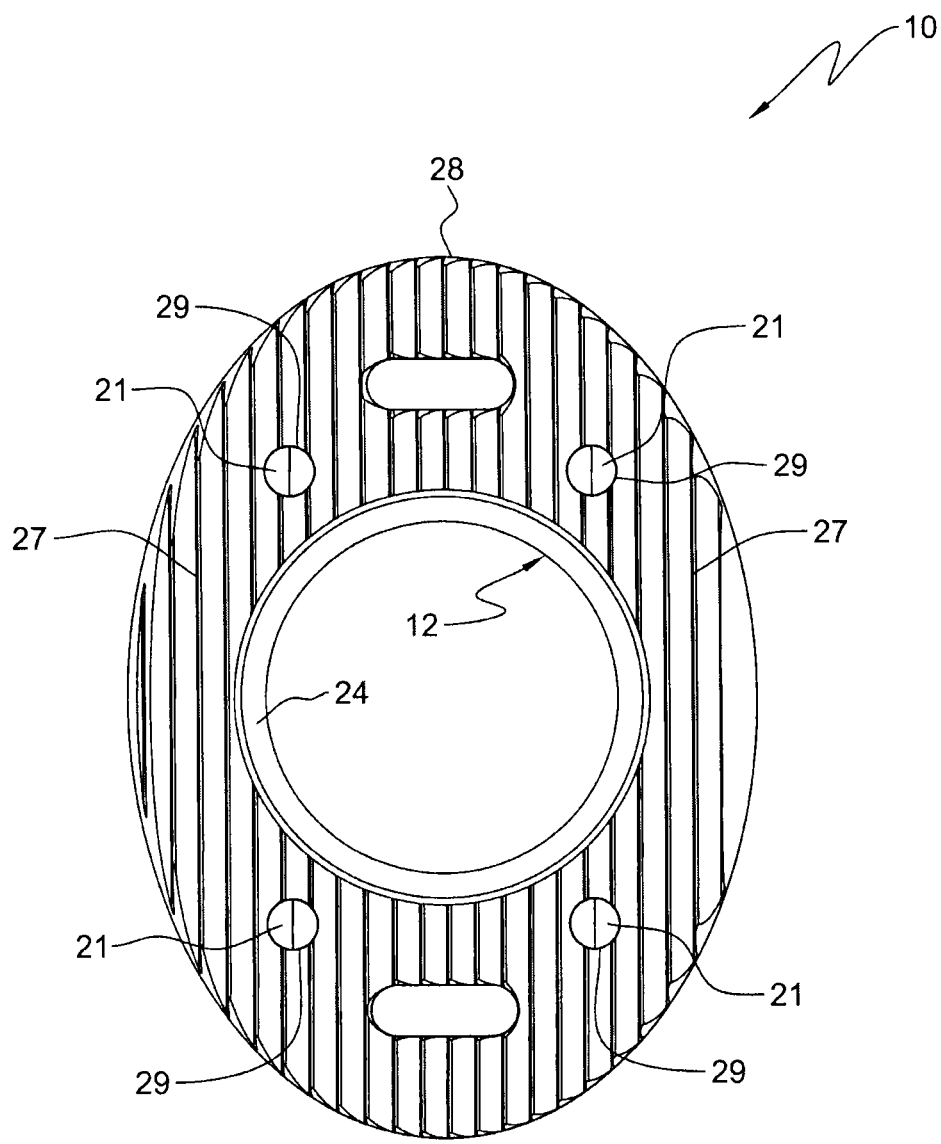
FIG. 7 is a bottom plan view of the intervertebral device shown in FIG. 1.
Figure 8:
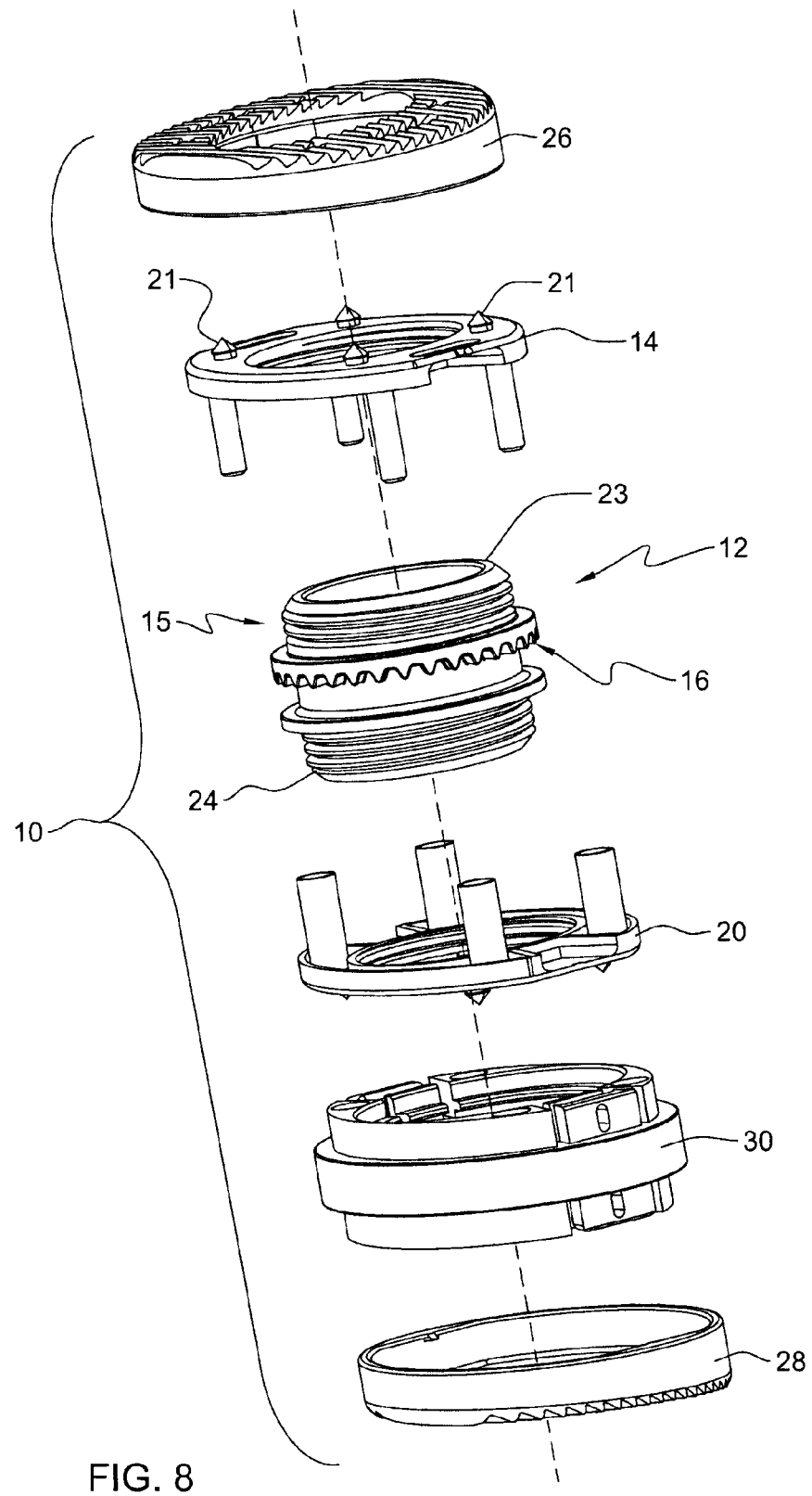
FIG. 8 is an exploded perspective view of the intervertebral device shown in FIG. 1.

FIG. 1 is a perspective view of an intervertebral device 10 according to one aspect of the invention. FIG. 2 is a front elevation view and FIG. 3 is a rear elevation of intervertebral device 10 shown in FIG. 1. FIG. 4 is a right side elevation view and FIG. 5 is a left side elevation view of intervertebral device 10 shown in FIG. 1. FIG. 6 is a top plan view and FIG. 7 is a bottom plan view of intervertebral device 10 shown in FIG. 1. FIG. 8 is an exploded perspective view of interverterbral device 10 shown in FIG. 1. As shown in FIGS. 1-8, intervertebral device 10 includes a cylindrical body 12 (shown most clearly in FIG. 8) at least one disk 14 mounted, for example, threaded to, cylindrical body 12, and means 16 for rotating cylindrical body 12 whereby at least disk 14 translates along cylindrical body 12 to vary the height 18 (see FIG. 2) of device 10. As shown most clearly in FIG. 8, disk 14 is mounted to cylindrical body 12 and may comprises a first disk 14, and device 10 may also include a second disk 20 mounted to the cylindrical body 12, for example, threadably mounted to cylindrical body 12.

Figure 9:
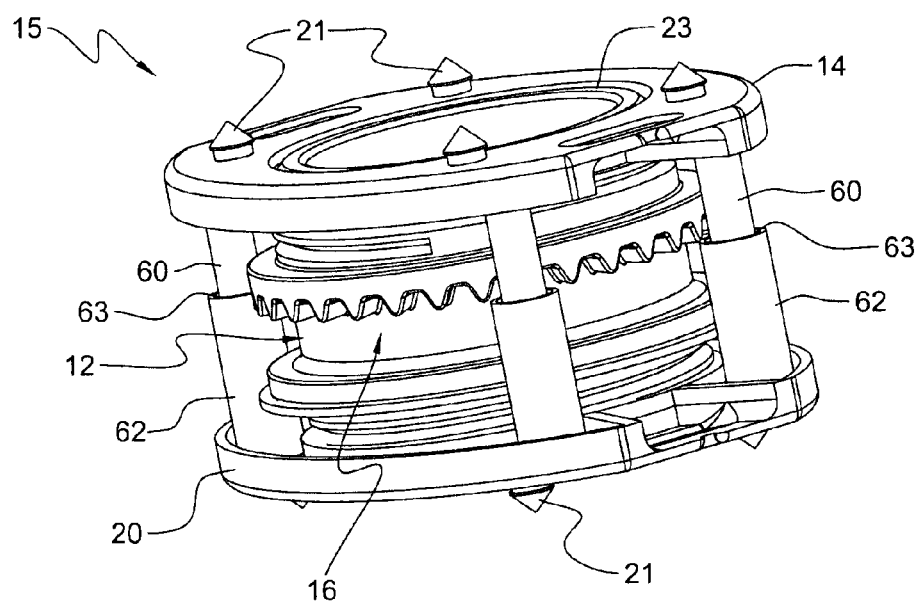
FIG. 9 is a perspective view of a subassembly having a cylindrical body and disk members according to one aspect of the invention.
Figure 10:
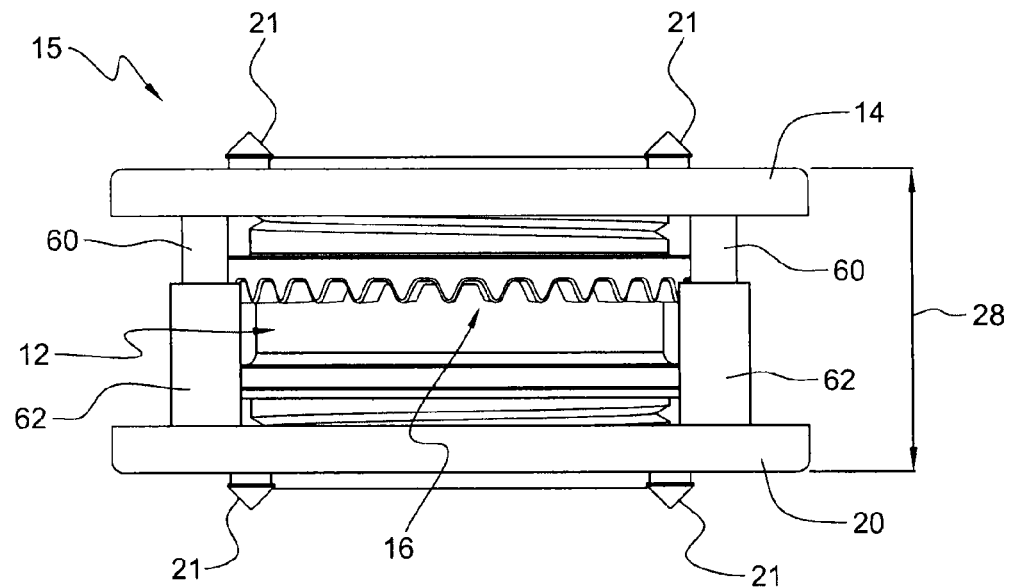
FIG. 10 is a front elevation view of the subassembly shown in FIG. 9.
Figure 11:
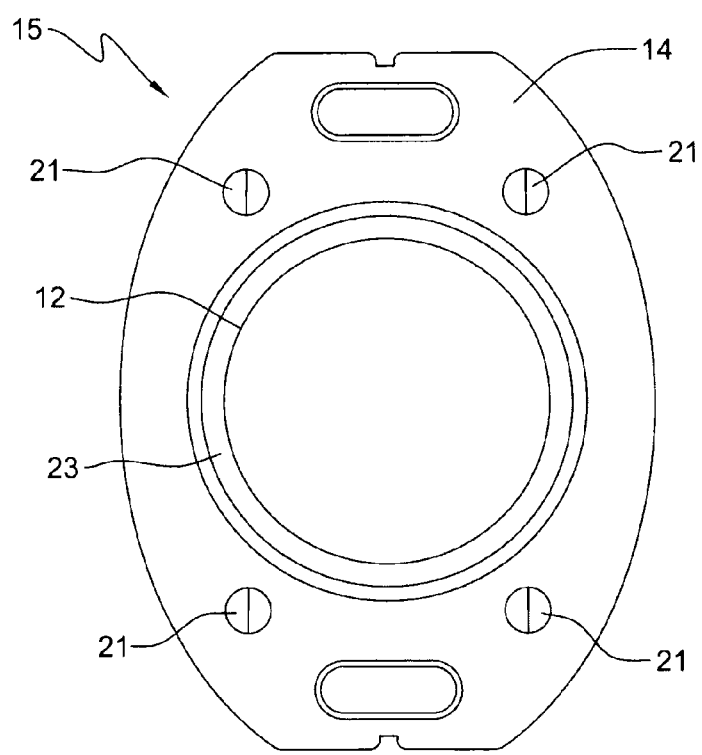
FIG. 11 is a top plan view of the subassembly shown in FIG. 9, the bottom plan view being substantially a mirror image thereof.
Figure 12:
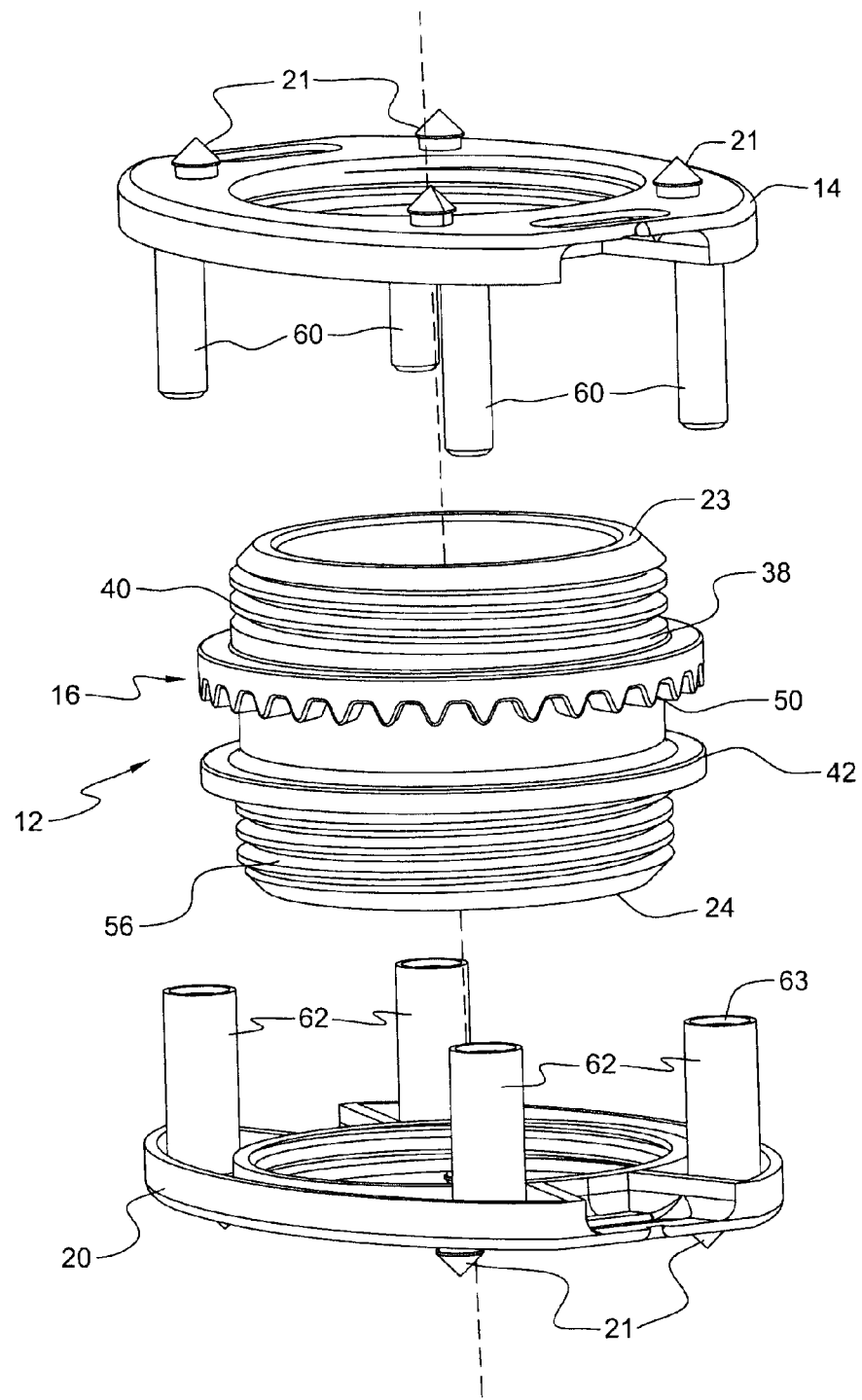
FIG. 12 is an exploded perspective view of the subassembly shown in FIG. 9.

FIG. 9 is a perspective view of a subassembly 15 or "cage" comprising cylindrical body 12, first disk 14, and second disk 20 according to one aspect of the invention. FIG. 10 is a front elevation view of subassembly 15 and FIG. 11 is a top plan view of subassembly 15 shown in FIG. 9. FIG. 12 is an exploded perspective view of subassembly 15 shown in FIG. 9. As shown in FIGS. 9-12, first disk 14 and second disk 20 may typically be threaded to cylindrical body 12, for example, first disk 14 may be threaded to a first end 23 of body 12 and second disk 14 may be threaded to second end 24 of body 12.

In one aspect of the invention, device 10 may comprise subassembly 15 having cylindrical body 12 and at least one first disk 14 or second disk 20 mounted for translation along cylindrical body 12, and means for translating first disk 14 or second disk 20 to vary a height 28 (see FIG. 10). For example, subassembly 15 may be inserted between two vertebrae (not shown) and adjusted where first disk 14 contacts a first vertebra and second disk 20 contacts a second vertebra to provide as spacer between the two vertebrae according to one aspect of the invention. However, since subassembly 15 is typically inserted inside a body, subassembly 15 may typically be enhanced to, among other things, facilitate handling and adjustment and enhance engagement with, for example, vertebrae.

Accordingly, one aspect of the invention may include one or more vertebrae engagement members (or end caps) and may also include a housing. This aspect of the invention is illustrated in FIGS. 1-8. As shown most clearly in FIG. 8, in one aspect, device 10 may comprise subassembly 15 having at least one, but typically, two, vertebra engagement members (or end caps) 26, 28. Engagement member 26 may typically be mounted to disk 14 and engagement member 28 may typically be mounted to disk 20. Disk 14 and 20 may include one or more recesses and/or projections to facilitate engagement and/or retention of engagement members 26, 28, for example, posts 21 adapted to be received by holes 29 in engagement members 26, 28. Engagement members 26, 28 may typically enhance the engagement of device 10 with vertebrae, for example, engagement members 26, 28 may be made from an elastomeric or plastic material (for example, polyether ether ketone (PEEK)), and have a plurality of ridges 27 adapted to enhance engagement with bone. Further details of engagement members or end caps 26 and 28 are provided in FIGS. 17 and 18 below.

As also shown most clearly in FIG. 8, in one aspect, device 10 may comprise a housing 30 mounted about subassembly 15. Housing 30 may comprise a cylindrical structure that surrounds subassembly 15. Housing 30 may, in some aspects, enhance the ability of the surgeon to hold and handle device 10, may protect subassembly 15 from debris or from damage, or may minimize or prevent contact of subassembly 15 by the surgeon or body parts. Housing 30 may be fabricated from metal, plastic, or an elastomer. Further details of housing 30 are provided in FIGS. 20 and 21 below.

Device 10 may also include means 16 for rotating cylindrical body 12 whereby at least one of disk 14 and disk 20 translates along cylindrical body 12 to vary the height 18 (see FIG. 2). As shown in FIG. 8, means 16 may include at least one, but typically, a plurality of projections mounted on cylindrical body 12, for example, a plurality of circumferential gear or rack teeth, that can, for example, be engaged by tool to rotate cylindrical body 12. Further details of means 16 are provided in FIGS. 14-16 below.

As shown in FIG. 12, cylindrical body 12 may comprise one or more cylindrical members. For example, as shown, cylindrical body 12 may comprise a single member. As shown in FIG. 12, cylindrical body 12 may typically comprise a hollow cylinder 38 having an upper external thread 40, lower external thread 56, and a lip, flange, or annular projection 42. As is typical of aspects of the invention, cylindrical body 12 may also have means 16 for rotating cylindrical body 12, for example, at least one, but typically, a plurality of projections 50. Thread 56 may be in the same or opposite hand of external thread 40. In one aspect, thread 40 and 56 are of opposite hand whereby rotation of cylindrical body 12 translates disks 14 and 20 in opposing or opposite axial directions. In one aspect, thread 40 and 56 may be an internal thread.

Cylindrical body 12 may also include a plurality of members which may be engaged to minimize or prevent relative rotation between members. For example, the two or more members (not shown) may include anti-rotation devices, may be keyed, or may be secured or fixed to each other. However, cylindrical body 12 may be a single integral part (as shown) or may comprise two or more subcomponents.

According to one aspect of the invention, cylindrical body 12 may be encased by housing 30. This aspect of the invention is most clearly illustrated in the cross section of device 10 shown in FIG. 13.

Figure 13:
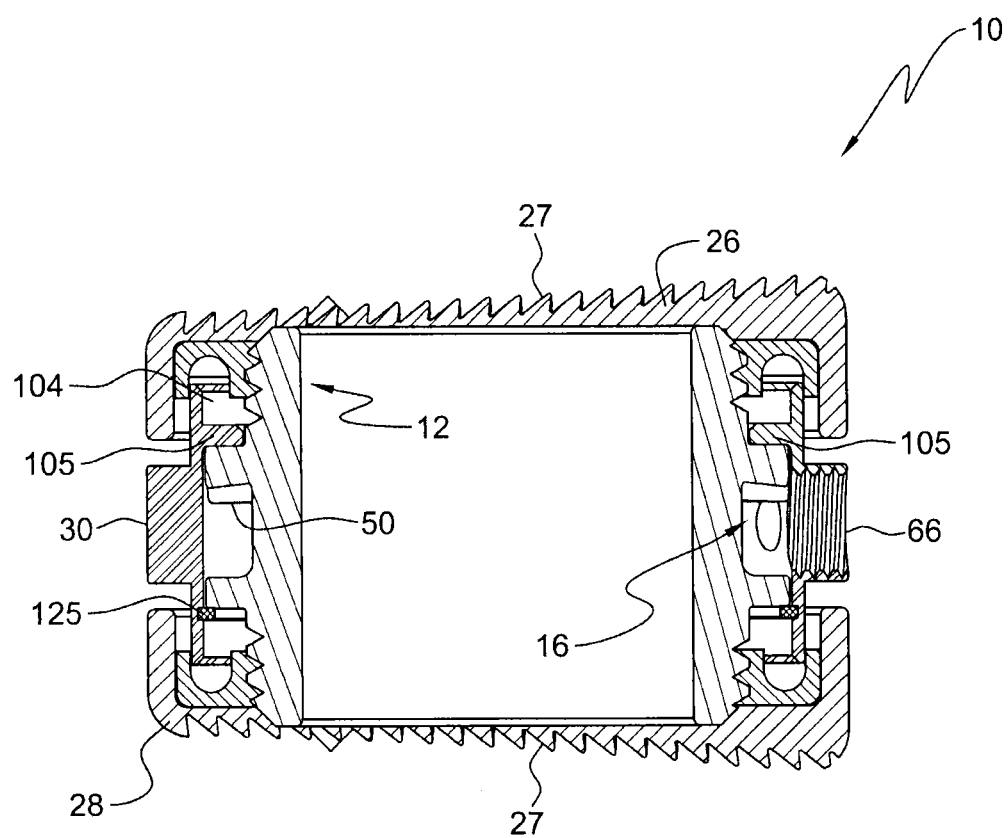
FIG. 13 is a cross sectional view of the device shown in FIG. 6 as viewed along section lines 13-13 in FIG. 6.

FIG. 13 is a cross section of device 12 shown in FIG. 6 as viewed along section lines 13-13 in FIG. 6. As shown in FIG. 13, cylindrical body 12 may be encased or surrounded by housing 30, for example, housing 30 may typically provide support, guide, or bearing surfaces upon which cylindrical body 12 bears, for example, when cylindrical body 12 is rotated according to aspects of the invention. Though cylindrical body 12 and housing 30 may be engaged in any conventional manner, for example, while allowing cylindrical body 12 to rotate relative to housing 30, in one aspect, cylindrical body 12 may be retained in housing 30 by one or more rings 125, for example, one or more snap rings, as is known in the art. In the aspect shown in FIG. 13, cylindrical body 12 is retained in housing 30 between annular lip 105 on housing 30 and snap ring 125 engaged in an annular recess 107 in housing 30.

Figure 15:
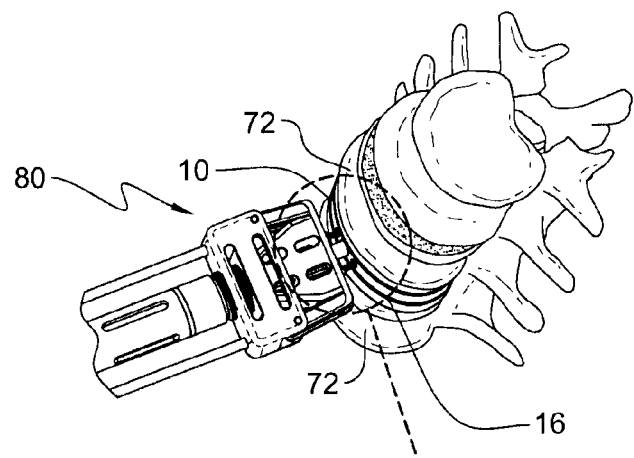
FIG. 15 is a top plan view of the method shown in FIG. 14.
Figure 16:
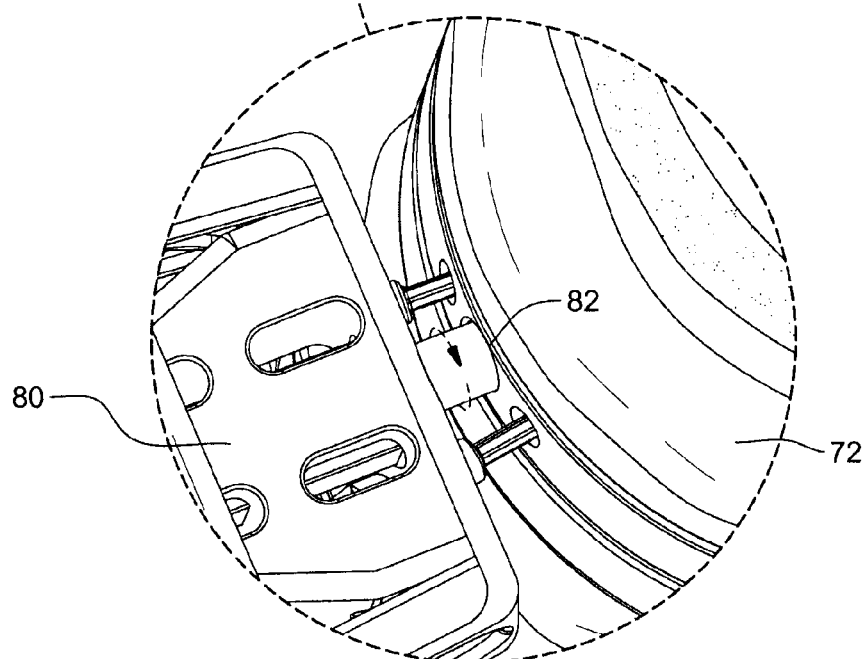
FIG. 16 is a detailed view of the engagement of a tool with the device as shown in FIG. 15.

FIGS. 12 and 13 also illustrate means 16 for rotating cylindrical body 12, for example, a plurality of projections 50. Projections 50 may comprise a plurality of evenly spaced gear teeth or rack teeth engageable and rotatable by an appropriate tool, for example, a tool having a pinion gear driven by the tool (see, for example, FIGS. 14-16) As shown in the cross section of FIG. 13, teeth 50 may be accessible through an aperture or hole 66 in housing 30. One tool that may be used to rotate cylindrical body 12 is illustrated in FIGS. 14, 15, and 16.

Cylindrical body 12 may be made from any material structural material that is compatible with bodily fluids. For example, cylindrical body 12 may be metallic, for example, made from stainless steel, cobalt chrome, titanium, or combinations thereof; may be made from plastic, for example, a durable polymer, for instance, an acetal resin, such as, DuPont's Delrin® acetal resin, or other suitable plastic; or a composite material, such as, PEEK.

Figure 14:
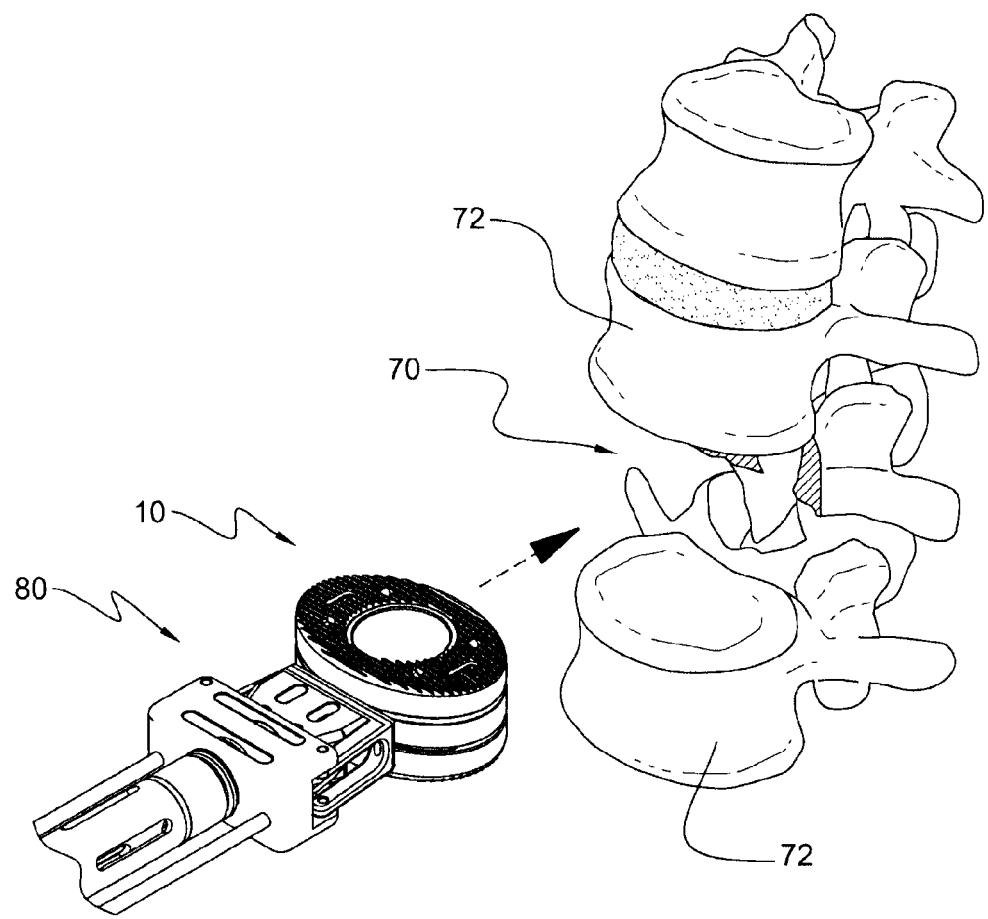
FIG. 14 is perspective view of a method of inserting the device shown in FIG. 1 into a spine with a typical tool.

As shown in FIG. 14, device 10 may be inserted into the a space 70 between two target vertebra 72 using a surgical instrument 80, for example, inserted through a skin opening (not shown). FIGS. 15 and 16 illustrate the use of instrument 80 to insert device 10 into space 70. As shown in FIG. 16, instrument 80 includes drive pinion 82 that can be inserted into hole 66 in housing 30 of device 10 to engage teeth 50 on cylindrical body 12. According to aspects of the invention, the height 18 (FIG. 2) of device 10 can be varied by rotating pinion 82 in a clockwise or counter-clockwise direction to translate teeth 50 in a circumferential direction and rotate cylindrical body 12 and vary the height 18 of device 10, for example, to accommodate the desired spacing or support between vertebrae 72. Device 10 may also be surgically inserted between vertebrae 72 using other conventional instruments.

In one aspect of the invention, subassembly 15 may include means for minimizing or preventing the rotation of one or both of disks 14 and 20. For example, when cylindrical body 12 is rotated according to aspects of the invention and at least one of disk 14 and 20 is translated along cylindrical body 12, means are provided to prevent disks 14 and 20 from rotating while disks 14 and 20 translate. Rotation of disks 14 and 20 is preferably avoided, or prevented entirely, to avoid misalignment or displacement of disks 14 and 20 while the height 18 of subassembly 15 or the height 28 of device 10 is adjusted, for example, by a surgeon. In one aspect, subassembly 15 includes at least one projection or pin 60 that minimizes or prevents rotation of disk 14 and/or disk 20. For example, in one aspect, disk 14 may include one or more pins 60 that engage housing 30, for example, engage a hole or recess in housing 30 which obstructs movement of pin 60 and, accordingly, obstructs or prevents rotation of disk 14. In another aspect, disk 20 may include one or more pins 60 that engage housing 30 in a similar fashion, for example, either disk 14 or disk 20 may include pins 60, or both of disks 14 and 20 may include one or more pins 60 that, for example, engage housing 20.

As shown in FIGS. 10 and 12, in one aspect, disk 14 may include one or more pins 60 and disk 20 may include one or more sleeves 62 having an open ends 63 into which pins 60 slidably engage, for example, telescopically engage. In another aspect, disk 20 may include one or more pins 60 and disk 14 may include one or more sleeves 62 into which pins 60 slidably engage. Disk 14 or disk 20 may also include both pins 60 and sleeves 62 that engage corresponding pins 60 and sleeves 62 in other disk 14 or disk 20. According to aspects of the invention, the engagement of pins 60 in sleeves 62 may be less than 1 inch of engagement, and are typically engaged for only a fraction of an inch, due to the limited translation of disk 14 and/or disk 20 required in aspects of the invention.

Disks 14 and 20, pins 60 and sleeves 62 may be made from any material structural material that is compatible with bodily fluids. For example, disks 14 and 20, pins 60 and sleeves 62 may be metallic, for example, made from stainless steel, cobalt chrome, titanium, or combinations thereof; may be made from a plastic, for example, a rigid polymer, for instance, an acetal resin, such as, DuPont's Delrin® acetal resin, or another suitable plastic; or may be a composite, such as, PEEK.

In one aspect of the invention, subassemly 15 shown in FIGS. 8 and 9 may comprise an intervertebral device according to the present invention. However, in other aspects, subassembly 15 may be augmented to, among other things, enhance vertebra engagement, protect subassembly 15, and/or facilitate handling of subassembly 15. Specifically, subassembly 15 may be supplemented with members that enhance engagement with bone. As shown in FIG. 8, subassembly 15 may be supplemented with one or more vertebra engagement members (or end caps) 26 and 28. Though members 26 and 28 may be any structural member that mounts to disk 14 and/or 20, one engagement member that may be used for each of members 26 and 28 is shown in FIGS. 17 and 18.

Figure 17:
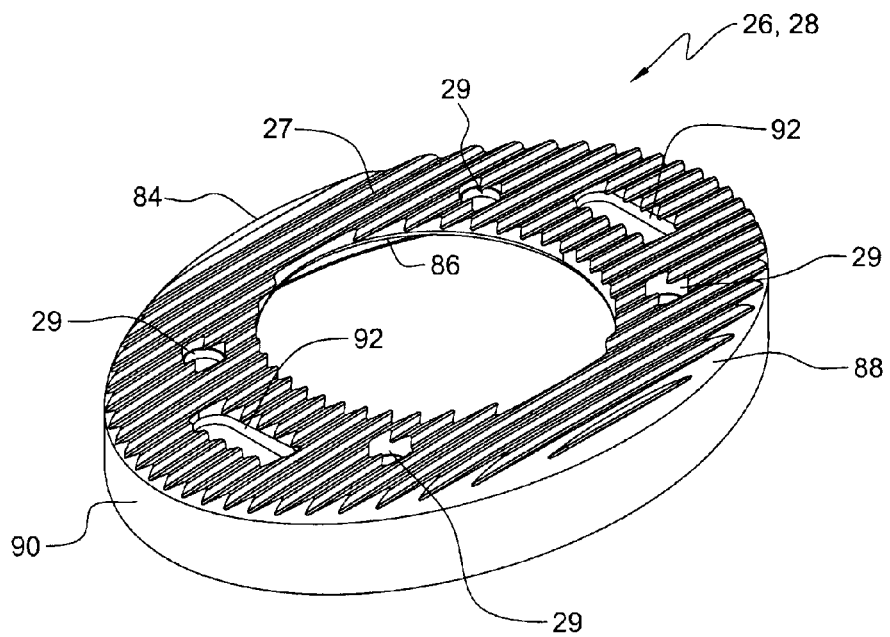
FIG. 17 is top perspective view of a vertebrae engagement member or end cap shown in FIG. 1 according to an aspect of the invention.
Figure 18:
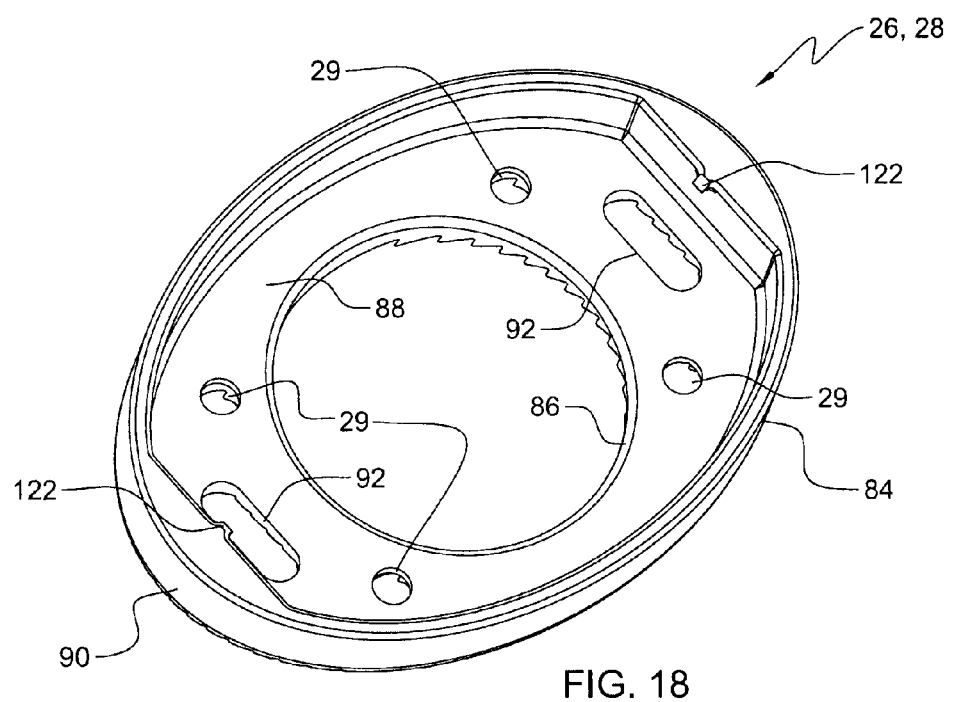
FIG. 18 is bottom perspective view of the vertebra engagement member or end cap shown in FIG. 17.

FIGS. 17 and 18 are a top perspective view and a bottom perspective view, respectively, of vertebra engagement members that can be used for members or end caps 26 and 28 shown in FIG. 8 according to one aspect of the invention. As shown, members 26 and 28 comprise a cap 84 having a top 88 and skirt 90 extending from top 88. Though the shape of cap 84 generally mimics the oval shape of subassembly 15, according to aspects of the invention, cap 84 may comprise any shape that is generally consistent with the shape of subassembly 15. For example, cap 84 may be round, square, or polygonal in shape. In addition, cap 84 may or may not include a skirt 90, however, in one aspect, skirt 90 is provided and provides a smooth transition about the edges of subassembly 15, for example, to facilitate handling.

As noted above, members 26 and 28 may be provided to enhance engagement of subassembly 15 with bone, for example, vertebrae. Accordingly, top 88 of cap 84 may include an substantially central opening 86 allowing access to the inside of device 10, a plurality of holes 29 and a plurality of holes 92. Holes 29 may be positioned and shaped to engage pins 21 on disks 14 and 20, for example, to position and retain members 26 and 28 on disks 14 and 20. Holes 92 may be provided to promote ingrowth of bone to enhance acceptance and retention of device 10. Holes 29 may be positioned to align with similar shaped holes in subassembly 15 and housing 30.

As noted above, members 26 and 28 may include a plurality of projections, ribs, or ridges 27 in top 88 that enhance engagement of members 26 and 28 with bone or other tissue. As shown in FIG. 17, ridges 27 may extend across a long dimension of cap 84, but may be directed in any direction with respect to cap 84, but are preferably oriented in a direction that enhances engagement with bone. For example, in one aspect, ridges 27 may be oriented substantially perpendicular the direction of insertion of device 10 whereby ridges 27 minimize the potential for device 10 to slide out of engagement with bone.

Figure 19:
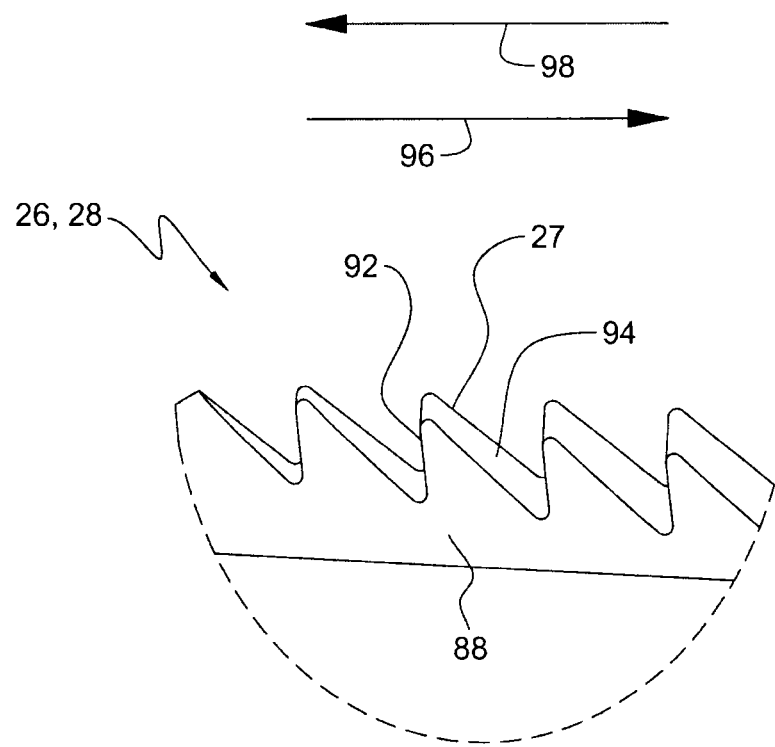
FIG. 19 is a detailed view of the device shown in FIG. 6 as identified by Detail 18 in FIG. 4.

The shape of ridges 27 may be any form that enhances engagement. For example, as shown in FIG. 19, ridges 27 may be substantially triangular in shape. FIG. 19 is detailed sided elevation view of member 26 shown in FIG. 4 identified as Detail 19 in FIG. 4. As shown in FIG. 19, ridges 27 may have a substantially vertical side 92 and a slanted side 94. The orientation of sides 92 and 94 of ridge 27 may facilitate insertion of device 10 in a direction indicated by arrow 96, but may resist movement of device 10 in a direction substantially opposite to the direction of insertion, as indicated by arrow 98. As also shown in FIG. 4, and suggested by FIG. 19, the height of cap 84 as indicated by height 100 in FIG. 4 may vary, for example, in a generally linear fashion as shown in FIG. 4, to again enhance engagement of device 10 with vertebrae and oppose dislodgment or movement of device 10 during insertion and while in use within the body.

Engagement members or end caps 26 and 28 may be made from any material that, for example, enhances the engagement of subassembly 15 with vertebrae. For example, members 26 and 28 may be metallic, for example, made from stainless steel or titanium; may be made from plastic, for example, a polyethylene, such as, an ultra-high molecular weight polyethylene (UHMWPE), a durable polymer, for instance, an acetal resin, such as, DuPont's Delrin® acetal resin, or another suitable plastic; or may be a composite, such as, PEEK.

As shown in FIG. 8, subassembly 15 may also be supplemented with one or more housings 30. Though housing 30 may be any structure that mounts to or accommodates subassembly 15, one housing 30 that may be used is shown in FIGS. 20 and 21.

Figure 20:
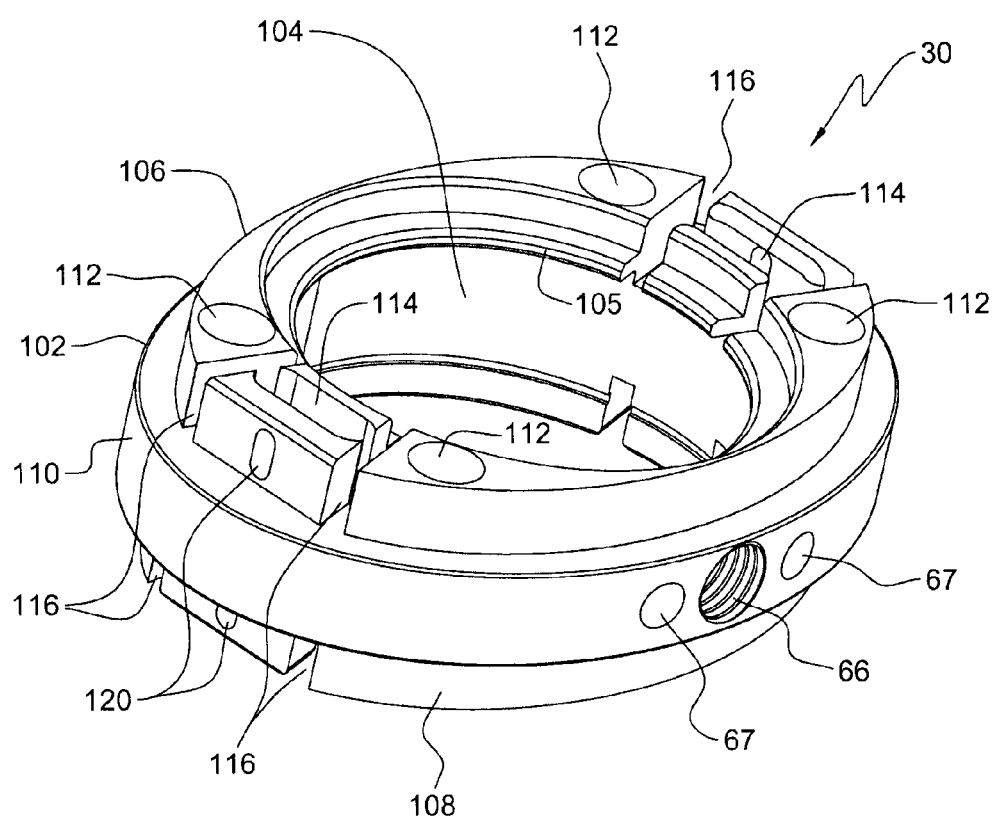
FIG. 20 top perspective view of a housing shown in FIG. 1 according to an aspect of the invention.
Figure 21:
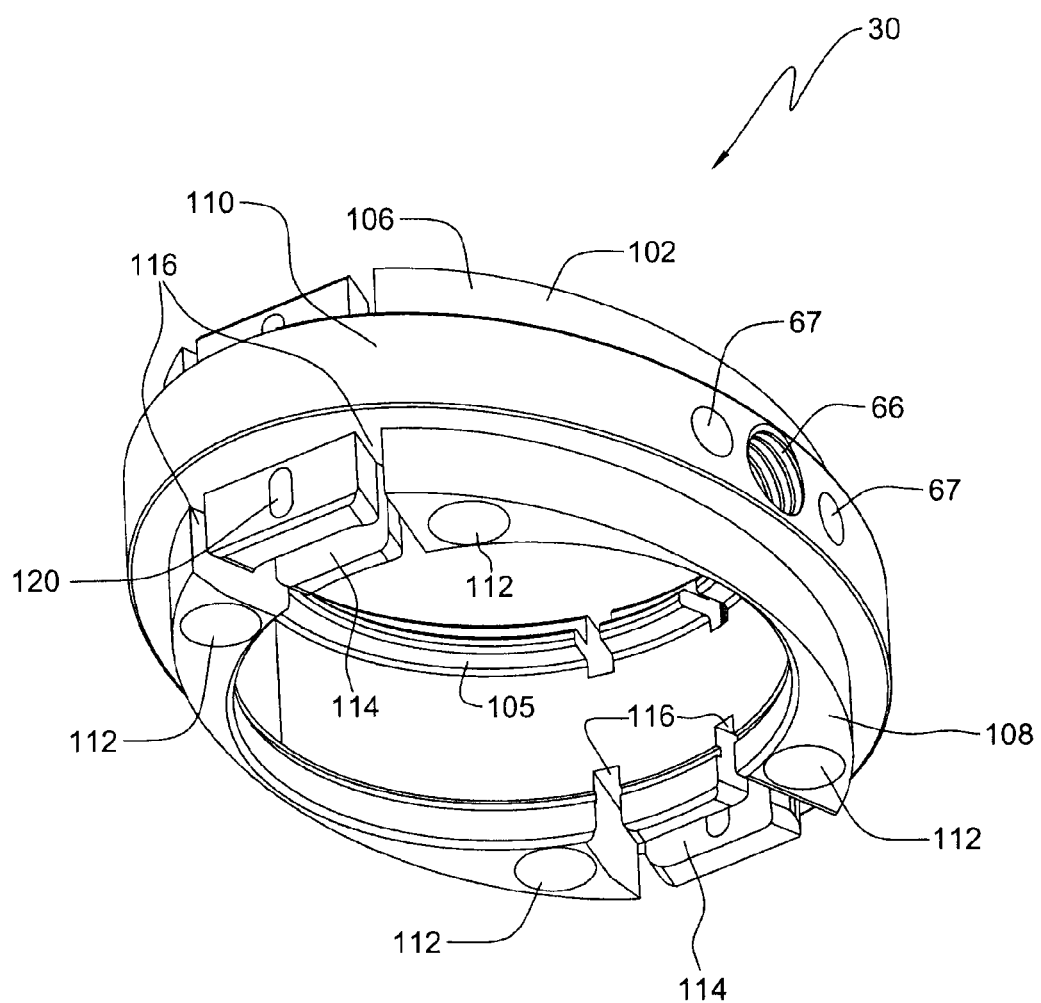
FIG. 21 is bottom perspective view of the housing shown in FIG. 19.

FIGS. 20 and 21 are a top perspective view and a bottom perspective view, respectively, of a housing 30 that can be used for housing 30 shown in FIG. 8 according to one aspect of the invention. As shown, housing 30 comprises a cylindrical body 102 having a substantially central through hole 104 that receives subassembly 15, for example, receives cylindrical body 12. Though the shape of body 102 generally mimics the oval shape of subassembly 15, according to aspects of the invention, body 102 may comprise any shape that is generally consistent with the shape of subassembly 15. For example, body 102 may be round, square, or polygonal in shape. In general body 102 may have any shape that accommodates subassembly 15 and, for example, provides some protection to subassembly 15 and may facilitate handling of device 10. As also shown in, through hole 104 may include at least one annular lip 105 and at least one annular recess 107. As shown most clearly in the cross section of FIG. 13, lip 105 may be provided to engage and or support cylindrical body 12 of subassembly 15.

As show in FIGS. 20 and 21, body 102 of housing 30 may include an upper boss or flange 106 and a lower boss or flange 108 that substantially define the height of body 102. Body 102 may also include a substantially annular rib 110 located between upper boss 106 and lower boss 108. Body 102 may include one or more through holes 112, for example, through holes 112 that accommodate the shape and structure of subassembly 15, for example, accommodate posts 61 and/or sleeves 62 of disks 14 and 20. Body 102 of housing 30 may include at least one hole or aperture 66 that permits access to the means 16 for rotating cylindrical body 12, for example, a tool adapted to engage a cylindrical gear rack as shown in FIGS. 14-16. For example, as shown in FIGS. 20 and 21, a threaded hole 66 may be substantially centrally located in annular rib 110 and be directed substantially radially.

Housing 30 may also include features that enhance engagement of subassembly 15 with bone, for example, vertebrae. Accordingly, body 102 may include a plurality of holes 114 and a plurality of slots 116 adapted to promote ingrowth of bone, such as, vertebrae, to promote acceptance and retention of device 10. Holes 114 may be positioned to align with similar shaped holes in subassembly 15 and in engagement members 26 and 28.

Housing 30 may be made from any material structural material that is compatible with bodily fluids. For example, housing 30 may be metallic, for example, made from stainless steel or titanium; may be made from plastic, for example, a polyethylene, such as, an ultra-high molecular weight polyethylene (UHMWPE), a durable polymer, for instance, an acetal resin, such as, DuPont's Delrin® acetal resin, or another suitable plastic; or may be a composite, such as, PEEK.

Aspects of the present invention may also include features that limit the movement or translation of at least one of disks 14 and 20. During adjustment of height 18 (see FIG. 2) of device 10, for example, during rotation of cylindrical body 12 by tool 80 (see FIGS. 14-16), in one aspect of the invention it is advantageous to limit the travel of disks 14 and 20. For example, typically, upon insertion of device 10 between vertebrae, for instance, as shown in FIGS. 14-16, the height 18 of device 10 may only be varied a fraction of an inch, for example, between about 0.010 inches to about 0.060 inches. Among other reasons, increasing the height 18 of device 10 beyond a typical predetermined limit may cause damage to surrounding tissue. Though subassembly 15 and housing 30 may include diverse features that somehow limit the travel of at least one of disks 14 and 20 while the height 18 of device 10 is being varied, FIG. 22 illustrates one aspect of the present invention for limiting travel of at least one disk 14 and 20.

Figure 22:
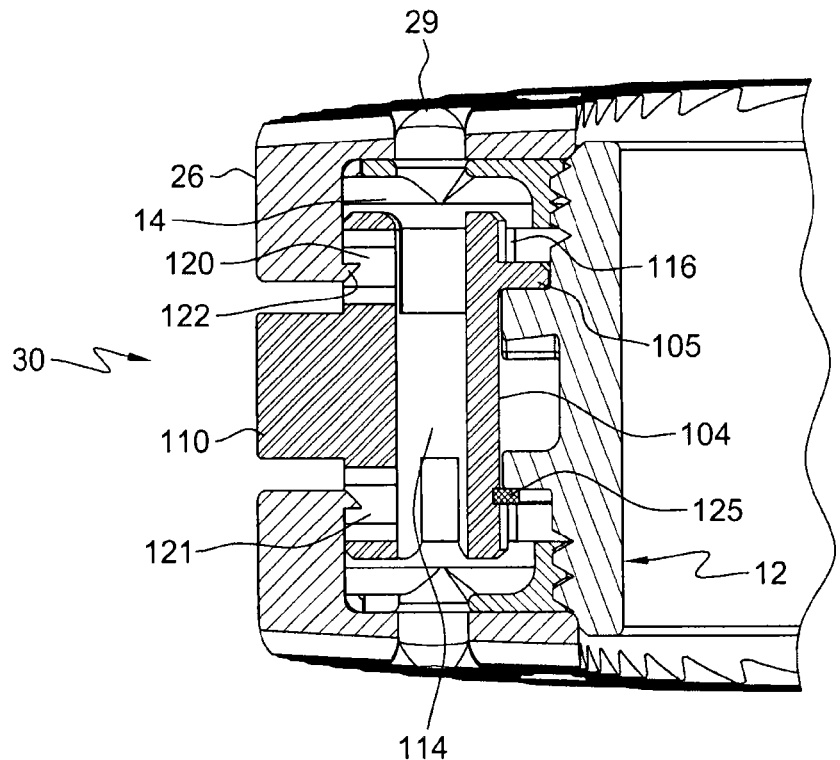
FIG. 22 is a cross sectional view of the device shown in FIG. 6 as viewed along section lines 22-22 in FIG. 6.

FIG. 22 is a detailed partial cross sectional view of device 10 as shown in FIG. 6 as indicated by section 22-22 in FIG. 6. FIG. 22 illustrates a partial cross sectional view of disk 14, engagement member (or end cap) 26, and housing 30. As shown in FIG. 22, in this aspect of the invention, housing 30 includes at least one recess, hole, or slot 120, but typically at least two recesses, holes, or slots 120, 121 positioned to engage at least one projection or tab 122 on engagement member 26. Projection 122 typically may include a chamfered edge that facilitates engagement of projection 122 with slot 120 and an opposing surface that contacts a surface of slot 122, for example, an end surface of slot 122, to limit the movement of projection 122 and the movement of engagement member 26. Since engagement member 26 is mounted to disk 14 of subassembly 15, limiting the movement of engagement member 26 effectively limits the movement, for example, the translation, of disk 14. A similar mechanism associated with slot 121 may limit the translation of engagement member 28 and disk 20 (both not shown in FIG. 22).

Figure 23A:
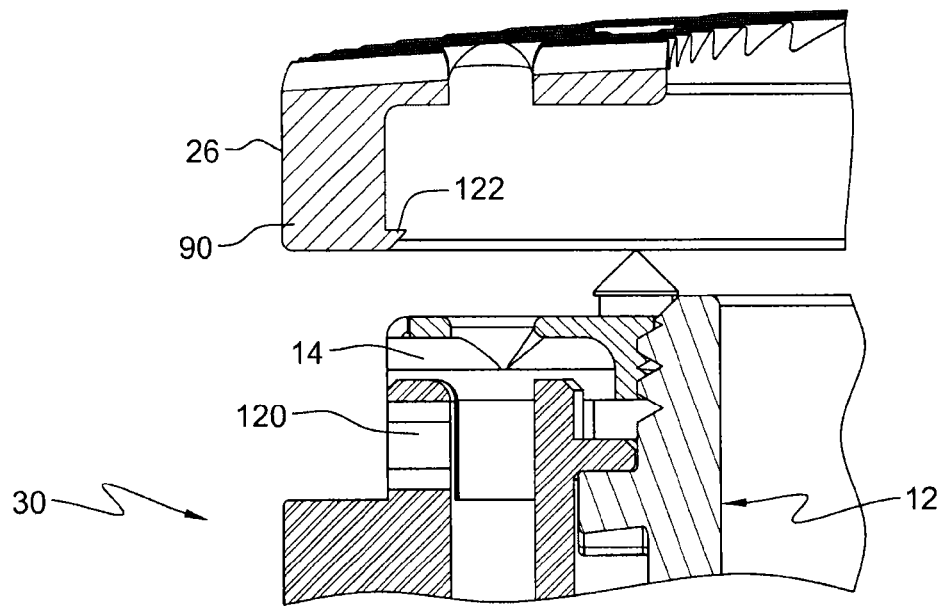
Figure 23B:
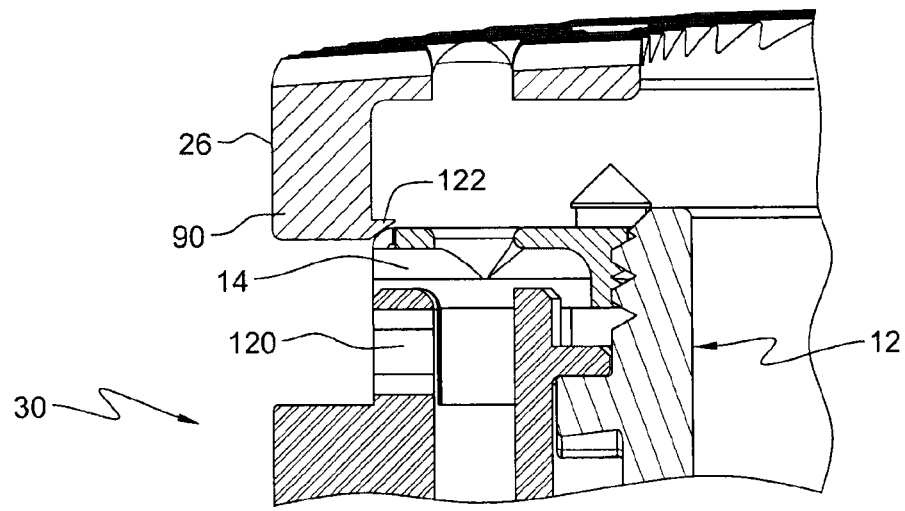
Figure 23C:
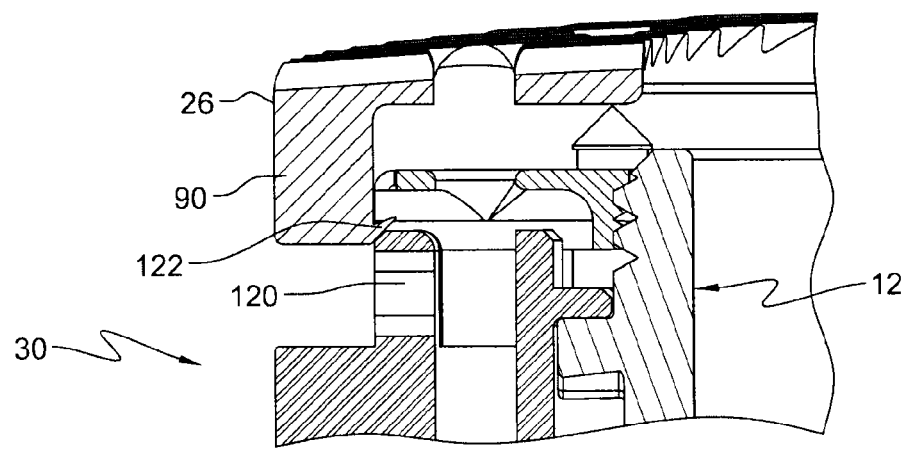
Figure 23D:
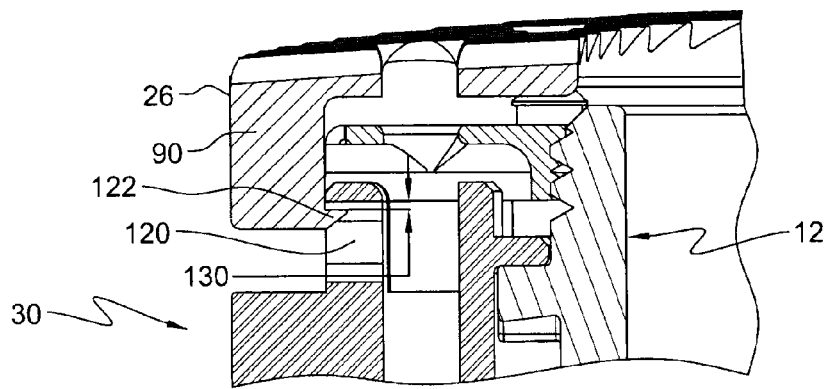

FIGS. 23A, 23B, 23C, and 23D illustrate a sequence of engagement of projection 122 of member 26 with slot 120 of housing 30 according to one aspect of the invention. In FIG. 23A, engagement member 26 lies above disk 14 and housing 30 where projection 122 is disengaged from disk 14 and housing 30. In FIG. 23B, member 26 initially makes contact with disk 14 where the chamfered surface of projection 122 engages disk 14 and is allowed to radially deflect projection 122 outward, for example, to deflect skirt 90 of member 26 radially outward. In FIG. 23C, engagement member 26 engages housing 30 and projection 122 continues to radially deflect. In FIG. 23D, engagement member 26 is substantially completely engaged with housing 30 where projection 122 penetrates slot 120 of housing 30 by being allowed to radially deflect inward due to the presence of slot 120. As shown in FIG. 23D, when deflected inward, the surface, for example, the upper surface, of slot 120, for example, without the assistance of a lead in chamfer on projection 122, interferes with the axial deflection of projection 122. According to aspects of the invention, projection 122, engagement member 26, and disk 14 can thus be limited to deflect in an axial direction, for example, upward in FIG. 23D. The deflection of disk 14 may be limited to a predetermined amount indicated by clearance 130 in FIG. 23D, for example, to between about 0.010 inches and about 0.100 inches. It will be apparent to those of skill in the art that projection 122 may be disengaged from slot 120 by deflecting projection 122 radially outward, for example, manually or with a tool, to permit removal of member 26.

Though only a single projection 122 and a single slot 120 are shown in FIGS. 22-23D, according to aspects of the invention, two or more engagements, such as, projection 122 with slot 120, may be positioned about device 10, for example, at opposite ends of device 10. In addition, 3 or more, or 4 or more, such engagement between a protection 122 and a slot 120 may be provided about the perimeter of device 10, for example, evenly distributed about the perimeter of device 10. One or more similar engagements may be provided between engagement member (or end cap) 28 and housing 30.

The size of device 10 may vary depending upon the dimensions of the application, for example, the size of the spine into which device 10 will be used. However, device 10 may typically have a height 18 (see FIG. 2) ranging from about 0.25 inches to about 3 inches, for example, between about 1 inch and about 2 inches. Device 10 may typically have a width or diameter 19 (see FIG. 2) ranging from about 0.5 inches to about 3 inches, for example, between about 0.5 inches and about 1.5 inches.

Aspects of the present invention provide devices and methods for stabilizing or replacing vertebra in a spine. As will be appreciated by those skilled in the art, features, characteristics, and/or advantages of the various aspects described herein, may be applied and/or extended to any embodiment (for example, applied and/or extended to any portion thereof).

Although several aspects of the present invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

The invention claimed is:

1. A variable height intervertebral device comprising:
   a cylindrical body having a first end and a second end opposite the first end;
   a first disk threaded to the first end of the cylindrical body and a second disk mounted to the second end of the cylindrical body;
   means for rotating the cylindrical body whereby the first disk translates along the cylindrical body to vary a height of the device;
   a plurality of pins mounted to one of the first disk and the second disk, and a plurality of sleeves mounted to the other of the first disk and the second disk, wherein the plurality of pins are slidably engageable with the plurality of sleeves, the plurality of pins and the plurality of sleeves inhibiting the first disk and the second disk from rotating when the means for rotating rotates the cylindrical body;
   a means for limiting translation of at least the first disk;
   a housing surrounding the cylindrical body and a first vertebra engagement member mounted to the first disk; and
   wherein the means for limiting translation comprises at least one recess in the housing and at least one projection on the first vertebra engagement member positioned to engage the at least one recess in the housing.

2. The device as recited in claim 1, wherein the means for rotating the cylindrical body comprises at least one projection positioned between the first end and the second end of the cylindrical body, the at least one projection deflectable by a tool.

3. The device as recited in claim 2, wherein the at least one projection comprises a plurality of circumferential teeth.

4. The device as recited in claim 3, wherein the plurality of circumferential teeth comprises at least one circumferential row of a plurality of gear teeth.

5. The device as recited in claim 1, wherein the plurality of pins comprises at least three pins and the plurality of sleeves comprises at least three sleeves.

6. The device as recited in claim 5, wherein the plurality of pins comprises at least four pins and the plurality of sleeves comprises at least four sleeves.

7. The device as recited in claim 1, wherein the device further comprises a second vertebra engagement member mounted to the second disk.

8. The device as recited in claim 7, wherein the first vertebra engagement member and the second vertebra engagement member are fabricated from one of a plastic and an elastomer.

9. The device as recited in claim 1, further comprising:
   an annular flange coupled to the cylindrical body between the first end and the second end.

10. A variable height intervertebral device comprising:
    a hollow cylindrical body having a threaded first end and a threaded second end opposite the threaded first end;
    a first disk internally threaded to the first end of the cylindrical body and a second disk internally threaded to the second end of the cylindrical body;
    a first end cap mounted to the first disk and a second end cap mounted to the second disk;

means for rotating the cylindrical body whereby the first disk axially translates along the cylindrical body and impels the first end cap into engagement with a first vertebra and the second end cap into engagement with a second vertebra;

a plurality of pins mounted to one of the first disk and the second disk and a plurality of sleeves mounted to the other of the first disk and the second disk, wherein the plurality of pins are slidably engageable with the plurality of sleeves, the plurality of pins and the plurality of sleeves inhibiting the first disk and the second disk from rotating when the means for rotating rotates the cylindrical body, a housing surrounding the cylindrical body, the housing comprises a recess; and wherein the first end cap comprises a projection and the projection is positioned to engage the recess in the housing to limit the translation of the first disk.

11. The device as recited in claim 10, wherein the means for rotating the cylindrical body comprises at least one projection positioned between the first end and the second end of the cylindrical body, the at least one projection engageable by a tool.

12. The device as recited in claim 11, wherein the at least one projection comprises a plurality of circumferential teeth engageable by a pinion of the tool.

13. The device as recited in claim 10, wherein the plurality of pins comprises at least two pins and the plurality of sleeves comprises at least two sleeves.

14. The device as recited in claim 10, wherein the means for rotating further causes the second disk to axially translate along the cylindrical body.

15. The device as recited in claim 10, further comprising:
an annular projection coupled to the hollow cylindrical body between the threaded first end and the threaded second end.

16. A method for separating vertebrae comprising:
inserting a variable height intervertebral device between a first vertebra and a second vertebra, wherein the variable height intervertebral device comprises:
a cylindrical body having a first end and a second end opposite the first end;
a first disk threaded to the first end of the cylindrical body and a second disk mounted to the second end of the cylindrical body;
a means for rotating the cylindrical body whereby the first disk translates along the cylindrical body to vary a height of the device;
a plurality of pins mounted to one of the first disk and the second disk, and a plurality of sleeves mounted to the other of the first disk and the second disk, wherein the plurality of pins are slidably engageable with the plurality of sleeves, the plurality of pins and the plurality of sleeves inhibiting the first disk and the second disk from rotating when the means for rotating rotates the cylindrical body; and
a means for limiting translation of at least the first disk;
a housing surrounding the cylindrical body and a vertebra engagement member mounted to the first disk; and
wherein the means for limiting translation comprises at least one recess in the housing and at least one projection on the vertebra engagement member positioned to engage the at least one recess in the housing; and
rotating the cylindrical body whereby at least the first disk axially translates along the cylindrical body between the first vertebra and the second vertebra.

17. The method as recited in claim 16, wherein the method further comprises limiting the axial translation of the first disk along the cylindrical body.

18. The method as recited in claim 16, wherein the method further comprises inhibiting the first disk from rotating when the means for rotating rotates the cylindrical body.

19. The method as recited in claim 16, wherein the means for rotating the cylindrical body comprises a plurality of circumferential teeth positioned about the cylindrical body, and wherein rotating the cylindrical body comprises engaging at least one of the teeth with a pinion mounted to a tool and deflecting the at least one of the teeth in a circumferential direction by rotating the pinion.

20. The method as recited in claim 16, wherein the variable height intervertebral device further comprises:
an annular flange coupled to the cylindrical body between the first end and the second end.

* * * * *

UNITED STATES PATENT AND TRADEMARK OFFICE
CERTIFICATE OF CORRECTION

PATENT NO. : 8,840,669 B2  
APPLICATION NO. : 13/258824  
DATED : September 23, 2014  
INVENTOR(S) : Farris et al.

Page 1 of 1

It is certified that error appears in the above-identified patent and that said Letters Patent is hereby corrected as shown below:

In the specification

Col. 1, Cross-Reference To Related Applications, Line 8: Delete "030869" and insert --030896--

Col. 1, Cross-Reference To Related Applications, Line 9: Delete "20," and insert --21,--

Col. 1, Cross-Reference To Related Applications, Line 10: Delete "2010/120728" and insert --2010/120782--

Col. 6, Detailed Description Of Figures, Line 50: Delete "subassemly" and insert --subassembly--

Col. 8, Detailed Description Of Figures, Line 1: Delete "102" and insert --12--

Signed and Sealed this  
Third Day of November, 2015

Michelle K. Lee  
*Director of the United States Patent and Trademark Office*